US008192990B2

(12) United States Patent
Riemen et al.

(10) Patent No.: US 8,192,990 B2
(45) Date of Patent: *Jun. 5, 2012

(54) BUFFER SOLUTION FOR ELECTROPORATION AND A METHOD COMPRISING THE USE OF THE SAME

(75) Inventors: Gudula Riemen, Langenfeld (DE); Elke Lorbach, Cologne (DE); Juliana Helfrich, Glauchau (DE); Gregor Siebenkotten, Frechen-Koenigsdorf (DE); Herbert Mueller-Hartmann, Cologne (DE); Kirsten Rothmann-Cosic, Berlin (DE); Corinna Thiel, Cologne (DE); Meike Weigel, Cologne (DE); Heike Wessendorf, San Francisco, CA (US); Helmut Brosterhus, Kirchhundern (DE); Michael Nix, Cologne (DE)

(73) Assignee: Lonza Cologne GmbH, Cologne (DE)

( * ) Notice: Subject to any disclaimer, the term of this patent is extended or adjusted under 35 U.S.C. 154(b) by 17 days.

This patent is subject to a terminal disclaimer.

(21) Appl. No.: 13/009,024

(22) Filed: Jan. 19, 2011

(65) Prior Publication Data

US 2011/0117654 A1    May 19, 2011

Related U.S. Application Data

(60) Division of application No. 11/931,886, filed on Oct. 31, 2007, now abandoned, which is a continuation of application No. 10/475,967, filed as application No. PCT/DE02/01483 on Apr. 23, 2002, now Pat. No. 7,332,332.

(30) Foreign Application Priority Data

Apr. 23, 2001   (DE) ................................ 101 20 000

(51) Int. Cl.
 *C12N 15/87* (2006.01)
 *C12N 13/00* (2006.01)
(52) U.S. Cl. ................... 435/461; 435/173.5; 435/173.6
(58) Field of Classification Search .......................... None
See application file for complete search history.

(56) References Cited

U.S. PATENT DOCUMENTS

| 829,633 | A | 8/1906 | Decker |
|---|---|---|---|
| 2,109,108 | A | 2/1938 | Fester |
| 4,850,759 | A | 7/1989 | Strand et al. |
| 4,964,762 | A | 10/1990 | Arai et al. |
| 34,256 | A | 5/1993 | Strand et al. |
| 5,574,019 | A | 11/1996 | Segall et al. |
| 5,780,272 | A | 7/1998 | Jarrell |
| 5,899,642 | A | 5/1999 | Berglow et al. |
| 5,965,543 | A | 10/1999 | Campisi et al. |
| 6,184,254 | B1 | 2/2001 | Bukoski et al. |
| 6,303,379 | B1 | 10/2001 | Selden et al. |
| 6,492,103 | B1 | 12/2002 | Taylor |
| 6,582,928 | B1 | 6/2003 | Ashkenazi et al. |
| 6,927,286 | B1 | 8/2005 | Shen et al. |
| 6,977,296 | B2 | 12/2005 | Kim |
| 7,014,990 | B2 | 3/2006 | Polyak et al. |
| 2002/0151563 | A1 | 10/2002 | Kajiji |
| 2003/0065039 | A1 | 4/2003 | Kharazmi et al. |
| 2003/0127621 | A1 | 7/2003 | Goldstein et al. |
| 2005/0064596 | A1 | 3/2005 | Riemen et al. |
| 2007/0110736 | A1 | 5/2007 | Riemen et al. |
| 2008/0113436 | A1 | 5/2008 | Riemen et al. |
| 2008/0145938 | A1 | 6/2008 | Riemen et al. |

FOREIGN PATENT DOCUMENTS

| EP | 0414551 | 2/1991 |
|---|---|---|
| WO | WO 9118103 A1 | 11/1991 |
| WO | WO-94/08602 | 4/1994 |
| WO | WO-95/06129 | 3/1995 |
| WO | WO-95/35389 | 12/1995 |
| WO | WO-99/13719 | 3/1999 |
| WO | WO-02/00871 | 1/2002 |

OTHER PUBLICATIONS

Neumann et al. Gene transfer into mouse lyoma cells by electroporation in high electric fields. The EMBO Journal, vol. 1, No. 7, pp. 841-845, 1982.*
Klenchin et al. Electrically induced DNA uptake by cells is a fast process involving DNA electrophoresis. Biophysical Journal, vol. 60, No. 4, pp. 804-811, 1991.*
Anderson et al., "Electroporation of Lymphold Cells Factors Affecting the Efficency of Transfection" *J. Biochem. Biophys. Meth.*, 1991; 22:207-22 (Exhibit 7).
Potter et al., "Enhancer-dependent Expression of Human x Immunoglobulin Genes Introduced into Mouse Pre-B Lymphocytes by Electroporation." *Proc. Natl. Acad. Sci. USA*, 1984; 81: 7161-5 (Exhibit 14).
Fromm et al., "Stable Transformation of Maize after Gene Transfer by Electroporation" *Nature*, 1986; 319: 791-3 (Exhibit 10).
Riggs et al., "Stable transformation of Tobacco by Electroporation: Evidence for Plasmid Concatenation" *Proc. Natl. Acad. Sci. USA*, 1986; 83: 5602-6 (Exhibit 15).
Yan et al., "High-Voltage and High-Salt Buffer Facilitates Electroporation of Human Aortic Smooth-Muscle Cells," *BioTechniques*, 1998; 24: 590-2 (Exhibit 20).
Friedrich et al., "High Efficiency Electrotransfection with Aluminum Electrode Using Microsecond Controlled Pulses" *Bioelectrochem. and Bioenerg.*, 1998; 47: 103-11 (Exhibit 9).
Xie and Tsong, "Study of Mechanisms of Electric Field-Induced DNA transfection v Effects of DNA Topology on Surface binding, Cell Uptake, Expression, and Integration into Host Chromosomes of DNA in the Mammalian Cell" *Biophys. J.*, 1993; 65: 1684-9 (Exhibit 19).

(Continued)

*Primary Examiner* — Jennifer Dunston
(74) *Attorney, Agent, or Firm* — Leydig, Voit & Mayer, Ltd.

(57) ABSTRACT

A method for introducing biologically active molecules into animal or human cells using an electric current includes suspending the cells and dissolving the biologically active molecules in a buffer solution including HEPES and at least 10 mmol$\times$l$^{-1}$ magnesium ions (Mg$^{2+}$), the buffer solution having a buffer capacity of at least 20 mmol$\times$l$^{-1}$ $\times$pH$^{-1}$ at a change in the pH from pH 7 to pH 8 and at a temperature of 25° C., and an ionic strength of at least 200 mmol$\times$l$^{-1}$. An electric voltage is applied to the suspension.

9 Claims, 6 Drawing Sheets

OTHER PUBLICATIONS van den Hoff et al., "Electrotransfection with 'Intracellular' Buffer" *Methods in Mol. Biol.*, 1995; 48 (15): 185-197 (Exhibit 18).

Fromm et al., "Expression of Genes Transferred into Monocot and Dicot Plant Cells by Electroporation" *Proceedings of the National Academy of Sciences USA*, 1985, 82:5824-8 (Exhibit 11).

Bolzacchini, Ezio et al., "Purification of Phleum Preatense Pollen Extract by Immunoaffinity Chromatography and High-performance Ion-exchange Chromatography," *Journal of Chromatography*, 1991, 548:229-34 (Exhibit B).

Rols, Marie-Pierre and Justin Teissie, "Ionic-strength Modulation of Electrically Induced Permeabiliazation and Associated Fusion of Mammalian Cells," *European Journal of Biochemistry*, 1989, 14:35-42 (Exhibit 16).

Tishchenko, Galina A. et al., "Effect of Salt concentration Gradient on Separtion on Different Types of Specific Immunoglobulins by Ion-exhcange Chromatography on DEAE Cellulose," *Journal of Chromatography B*. 1998, 706:157-66 (Exhibit 17).

Ye, Xiuyun et al., "Isolation of Lactoperoxidase, Lactoferrin, α-lactalbumin, β-lactoglobulin B and β-lactoglobulin A from Bovine Rennet Whey Using Ion Exchange Chromatography," *The International Journal of Biochemistry & Cell Biology*, 2000, 32:1143-50 (Exhibit 21).

Ullah et al. In Vivo and In Vitro Chernotactic Methylation in *Bacillus Subtilis*. *Joural of Bacteriology*, vol. 145, No. 2, pp. 958-965, Feb. 1981.

Hartikka et al. Sodium Phosphate Enhances Plasmid DNA Expression in Vivo. *Gene Ther*. vol. 7, No. 14, pp. 1171-1182, Jul. 2000.

Alberts et al. "Molecular Biology of the Cell", 3rd Ed. New York: Garland Publishing Inc., 1994, p. 508.

Kariko et al. Phosphate-enhanced Transfection of Cationic Lipid-complexed mRNA and Plasmid DNA. Biochim Biophy Acta. vol. 1369, No. 2, pp. 320-334, Mar. 1998.

Cambrex Catalog Entry for DMEM High Gluose, with L-glutamine, printed from http://www.cambrex.com on Jan. 6, 2005.

Shimizu et al.,"Application of electrofusion on the gene transfer and hybridoma production", (1986) Med. Immunol. 11, pp. 105-110.

Tekle et al. Selective and asymmetric molecular transport across electroporated cell membranes. Proceedings of the National Academy of Sciences of the USA. vol. 91, pp. 11512-11516, 1994.

Myers et al. The dual-specificty CIK kinase induces neuronal differentiation of PC12 cells. Molecular and Cellular Biology, vol. 14, No. 10, pp. 6954-6961, Oct. 1994.

Wong et al. Involvement of p90rsk in neurite outgrowth mediated by the cell adhesion molecule I 1. The Journal of Biological Chemistry, vol. 271, No. 30, pp. 18217-18223, 1996.

Izutsu et al. Decreased protein-stabilizing effects of cryoprotectants due to crystallization, Pharmaceutical Research, vol. 10, No. 8, pp. 1232-1237, 1993.

Chu et al., "Electroporation for the efficient transfection of mammalian cells with DNA", Nucleic Acids Research, vol. 15, No. 3, 1311-1326, 1987.

* cited by examiner

Transfection efficiency and survival rate of primary human endothelial cells as a function of buffer capacity and ionic strength Transfection efficiency and survival rate of primary human lymphocytes as a function of buffer capacity and ionic strength Primary human fibroblasts (93 % H-2K$^k$-positive)

reference          transfected

Human smooth muscle cells (53.8% H-2K$^k$-positive)

reference    transfected

Primary human melanocytes
(56,2 % GFP-positive)

reference     transfected

Human CML cell line K562
(77,7 % GFP-positive)

reference                                   transfected

SEQUENCE LISTING

<160> NUMBER OF SEQ ID NOS: 6

<210> SEQ ID NO 1
<211> LENGTH: 16
<212> TYPE: PRT
<213> ORGANISM: Artificial sequence
<220> FEATURE:
<223> OTHER INFORMATION: Artificial peptide 1

<400> SEQUENCE: 1

Met Glu Glu Asp Thr Pro Pro Lys Lys Arg Lys Val Glu Asp Leu
1               5                   10                  15

<210> SEQ ID NO 2
<211> LENGTH: 20
<212> TYPE: PRT
<213> ORGANISM: Artificial sequence
<220> FEATURE:
<223> OTHER INFORMATION: Artificial peptide 2

<400> SEQUENCE: 2

Gly Lys Pro Thr Ala Asp Asp Gln His Ser Thr Pro Lys Lys Lys Arg
1               5                   10                  15

Lys Val Glu Asp
            20

<210> SEQ ID NO 3
<211> LENGTH: 20
<212> TYPE: PRT
<213> ORGANISM: Artificial sequence
<220> FEATURE:
<223> OTHER INFORMATION: Peptide nucleic acid (PNA 1), amino acid
      sequence

<400> SEQUENCE: 3

Gly Lys Pro Thr Ala Asp Asp Gln His Ser Thr Pro Lys Lys Lys Arg
1               5                   10                  15

Lys Val Glu Asp
            20

<210> SEQ ID NO 4
<211> LENGTH: 25
<212> TYPE: PRT
<213> ORGANISM: Artificial sequence
<220> FEATURE:
<223> OTHER INFORMATION: Peptide nucleic acid (PNA 2), amino acid
      sequence

<400> SEQUENCE: 4

Pro Ser Ser Asp Asp Glu Ala Thr Ala Asp Ser Gln His Ser Thr Pro
1               5                   10                  15

Pro Lys Lys Lys Arg Lys Val Glu Asp
            20                  25

<210> SEQ ID NO 5
<211> LENGTH: 13
<212> TYPE: DNA
<213> ORGANISM: Artificial sequence
<220> FEATURE:
<223> OTHER INFORMATION: Peptide nucleic acid (PNA), nucleic acid
      sequence

<400> SEQUENCE: 5 ctcttcctt ttc                                                    13

```
<210> SEQ ID NO 6
<211> LENGTH: 25
<212> TYPE: PRT
<213> ORGANISM: Artificial sequence
<220> FEATURE:
<223> OTHER INFORMATION: Artificial peptide 3

<400> SEQUENCE: 6

Pro Ser Ser Asp Asp Glu Ala Thr Ala Asp Ser Gln His Ser Thr Pro
1               5                   10                  15

Pro Lys Lys Lys Arg Lys Val Glu Asp
            20                  25
```

BUFFER SOLUTION FOR ELECTROPORATION AND A METHOD COMPRISING THE USE OF THE SAME

CROSS REFERENCE TO RELATED APPLICATIONS

This is a divisional of U.S. patent application Ser. No. 11/931,886, filed on Oct. 31, 2007, which is a continuation of U.S. patent application Ser. No. 10/475,967, now U.S. Pat. No. 7,332,332, filed on Jan. 8, 2004, which is a U.S. National Phase application under 35 U.S.C. §371 of International Application No. PCT/DE2002/001483; filed on Mar. 23, 2002, and claims the benefit of German Patent Application No. DE 101 20 000.5, filed on Apr. 23, 2001. The International Application was published in German on Oct. 31, 2002 as WO 02/086134 A1 under PCT Article 221(2)

BACKGROUND

The introduction of biologically active molecules, such as for example, DNA, RNA or proteins, into living cells is an important instrument for studying biological functions of these molecules. A preferred method for introducing foreign molecules into the cells is electroporation which, unlike other methods, only causes slight permanent changes to the biological structure of the target cell by the transfer reagents. During electroporation the foreign molecules are introduced into the cells from an aqueous solution by a brief current flow wherein the cell membrane is made permeable for the foreign molecules by the action of short electrical pulses. As a result of the "pores" briefly formed in the cell membrane, the biologically active molecules initially enter the cytoplasm in which they can already exert their function to be studied if necessary. In cases where DNA is introduced into eukaryotic cells, this must enter the cell nucleus however, so that it is possible for the genetic information to be expressed. In the case of dividing cells, this can take place during the cell division wherein the DNA passively enters the cell nucleus after the temporary dissolution of the nuclear membrane. In studies of quiescent or weakly dividing cells, for example, primary animal cells, however, the DNA does not enter into the cell nucleus in this way so that corresponding methods cannot be used here or at least are very tedious. Moreover, especially when DNA is introduced into animal cells, so-called transfection, particular problems frequently occur as a result of the lability of the cells, since the survival rate of the cells influences the efficiency of the transfection as an important parameter.

In the past cell culture media (Anderson et al. (1991), J. Biochem. Biophys. Meth. 22, 207) or salt solutions buffered with phosphate or HEPES (Potter et al. (1984), Proc. Natl. Acad. Sci. USA 81, 7161; Fromm et al. (1985), Nature 319, 791) were frequently used to take up the animal cells and DNA molecules. However, non-buffered or weakly buffered mannitol or saccharose solutions were also used during the electroporation of animal cells (Shimizu et al. (1986), Med. Immunol. 11, 105; Riggs et al. (1986), Proc. Natl. Acad. Sci. USA 83, 5602). Such non-buffered or weakly buffered solutions leads to an increased cell mortality and significantly reduced transfection efficiency as described in Yan et al. (1998), BioTechniques 24, 590.

Yan et al. (1998) describes the use of a buffer solution for electroporation consisting of 100 mM HEPES, 137 mM NaCl, 4 mM $Na_2HPO_4$ and 6 mM dextrose. Smooth muscle cells from human aorta could certainly be successfully transfected in this buffer but the transfection efficiency was only 15% with a survival rate of only 10 to 20%. Furthermore, the buffer used by Yan et al., is only optimised for voltage pulses up to 500 V so that no indication is given as to whether this buffer can also be used for higher voltage pulses such as are required for the direct transfection into the cell nucleus. In any case, however, the transfection efficiencies achieved in this buffer are too low to meet higher demands.

In many cases, buffers having a low ionic strength and therefore low conductivity were used in order to avoid cell damage as a result of high currents which was observed when using buffer solutions having high conductivity, especially during the application of longer high-voltage pulses.

Friedrich et al., 1998 (Bioelectrochem. and Bioenerg. 47, 103) describes that the current flow during electroporation leads to a change in the pH in the vicinity of the electrodes as a result of electrolysis of the water. This change in the pH causes the release of cytotoxic $Al^{3+}$ ions from the aluminium electrodes of the cuvettes and therefore causes increased cell mortality. The authors here propose a shortening of the pulse duration to increase the transfection efficiency. No information is given on any change to the buffer used.

Divalent cations such as $Mg^{2+}$ for example, can be added to the electroporation buffer. Magnesium ions facilitate the binding of DNA to the surface of the cells and thereby bring about an increased transfection rate. However, this only seems to apply for $Mg^{2+}$ concentrations up to 10 mM since at higher concentrations negative effects predominate, such as, for example, a reduction in the electrophoresis as a result of neutralisation of the charges of the DNA molecules or heating of the buffer as a result of an increase in the conductivity as described in Xie and Tsong (1993), Biophys. J. 65, 1684 and Neumann et al. (1982), EMBO J. 1, 841; Klenchin et al. (1991), Biophys. J.60, 804.

Furthermore, the buffer can be matched with regard to its composition to the intracellular conditions in order to increase the survival rate of the cells. Thus, a buffer having high potassium and low sodium concentrations corresponding to the cytoplasm can be used so as to prevent any collapse of the intracellular $Na^+/K^+$ ratio as a result of substance exchange via the pores formed in the cell membrane during the electroporation as described in van den Hoff et al. (1995), Methods in Mol. Biol. 48, Chapter 15, 185-197. However, this results in a reduction in the transfection efficiency for pulses having a field strength higher than 1300 V/cm.

All the buffer solutions described so far however have the disadvantage that the transfection efficiencies achieved when using them are relatively low and/or the buffers are not suitable for application during the electroporation of quiescent or weakly dividing cells.

SUMMARY

An aspect of the present invention is thus to provide a buffer solution for electroporation which makes it possible to achieve higher transfection efficiencies with a low cell mortality rate and to provide a corresponding method.

In an embodiment, the present invention provides a method for introducing biologically active molecules into animal or human cells using an electric current. The method includes suspending the cells and dissolving the biologically active molecules in a buffer solution including HEPES and at least 10 mmol×$l^{-1}$ magnesium ions ($Mg^{2+}$), the buffer solution having a buffer capacity of at least 20 mmol×$l^{-1}$ ×$pH^{-1}$ at a change in the pH from pH 7 to pH 8 and at a temperature of 25° C., and an ionic strength of at least 200 mmol×l$^{-1}$. An electric voltage is applied to the suspension.

BRIEF DESCRIPTION OF THE DRAWINGS

The invention will be described with respect to exemplary embodiments and drawings, in which.

DETAILED DESCRIPTION

Figure 1:
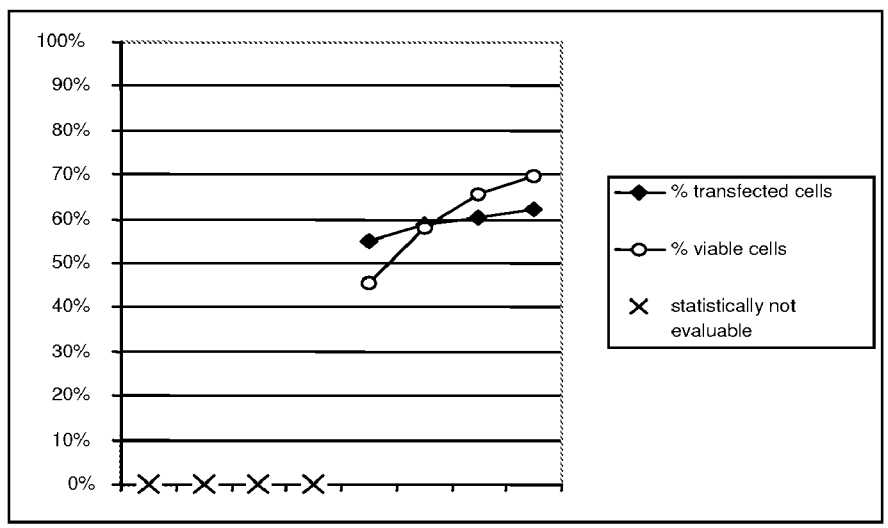
FIG. 1 is a graphical representation of the transfection efficiency and the survival rate for primary human endothelial cells as a function of the buffer capacity and the ionic strength of the buffer solution.
Figure 1:
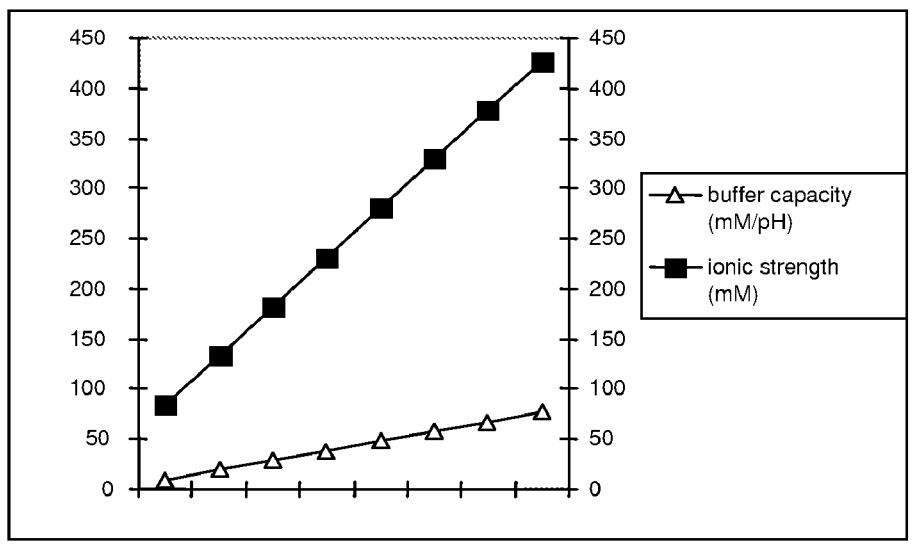

With the buffer solution of the present invention it is possible to introduce biologically active molecules into animal or human cells by means of electroporation with transfection efficiencies up to 93% and at the same time with low cell mortality. Various cell types can be successfully transfected in this buffer, especially quiescent and weakly dividing cells. Moreover, by using the buffer solution it is possible to use high-voltage pulses having a field strength of at least 2000 V/cm, which allows DNA molecules to be transfected directly into the cell nucleus of primary animal and human cells. A decisive factor for the advantageous properties of the buffer according to the invention is the combination of a high buffer capacity with a high ionic strength. The buffer capacity β describes the quantity of a proteolyte required to change the pH of a buffer solution by one pH unit (β=dC*dpH$^{-1}$ where dC=added amount of acid or base and dpH=change in the pH). The ionic strength I of a solution can be calculated using the formula I=0.5 Σc$_i$*z$_i^2$ (c$_i$=ion concentration in mol/l, z$_i$=ion charge). The "Java Buffer Calculator" program (Twigger & Beynon, 1998) was used to calculate the ionic strengths of the buffer substances given in this application. In this framework the buffer can be optimised in terms of its composition for the different cell types and requirements.

In an embodiment the buffer solution has a buffer capacity between 22 and 80 mmol*l$^{-1}$*pH$^{-1}$, preferably between 40 and 70 mmol*l$^{-1}$*pH$^{-1}$. The ionic strength may be in a range between 200 and 500 mmol*l$^{-1}$, or specifically between 250 and 400 mmol*l$^{-1}$. In general, there is thus an optimum in relation to buffer capacity and ionic strength, depending on the cell type and the other experimental conditions, there being an interaction between these two parameters.

In another embodiment the buffer solution contains at least 10 mmol*l$^{-1}$ magnesium ions (Mg$^{2+}$), preferably 15 to 20 mmol*l$^{-1}$ magnesium ions. Contrary to prior findings, it has surprisingly been found that Mg$^{2+}$ in the buffer according to the invention, even in fairly high concentrations, can bring about an increase in the transfection rate and to a significantly greater extent than could be explained by the simultaneous slight increase in the ionic strength. In this case, the buffer can contain magnesium chloride (MgCl$_2$) and/or magnesium sulphate (MgSO$_4$).

In an embodiment the buffer according to the invention can have a lower concentration of potassium ions (K$^+$), for example 2 to 6 mmol*l$^{-1}$ K$^+$, and a higher concentration of sodium ions (Na$^+$), for example 100 to 150 mmol*l$^{-1}$ Na$^+$, if compared with the cytoplasm of the cells. Thus, the buffer according to the invention is not matched to the intracellular Na$^+$/K$^+$ ratio but rather "extracellular" ratios are present in this respect. Surprisingly, however, this has no negative effects on the cells but nevertheless results in a significant increase in the transfection and cell survival rate.

The buffer according to the invention can include HEPES and/or Na$_2$HPO$_4$/NaH$_2$PO$_4$ as a buffer substance. However, Tris/HCl or K$_2$HPO$_4$/KH$_2$PO$_4$ can also be used as buffer substances. Furthermore, the buffer may also contain additional components, for example, sodium chloride, sodium succinate, mannitol, glucose, sodium lactobionate and/or peptides.

Six groups of buffer systems, each optimised to different cell types, are mentioned below as examples for compositions of the buffer solutions according to the invention. However, other compositions are also possible within the scope of the invention so that these examples should not be understood as a restriction.

1) 4-6 mM KCl, 10-20 mM MgCl$_2$ and 120-160 mM Na$_2$HPO$_4$/NaH$_2$PO$_4$ (pH 7.2)
2) 4-6 mM KCl, 10-20 mM MgCl$_2$, 5-25 mM HEPES and 120-160 mM Na$_2$HPO$_4$/NaH$_2$PO$_4$ (pH 7.2)
3) 4-6 mM KCl, 10-20 mM MgCl$_2$, 50-160 mM Na$_2$HPO$_4$/NaH$_2$PO$_4$ (pH 7.2) and 5-100 mM sodium lactobionate or 5-100 mM mannitol or 5-100 mM sodium succinate or 5-100 mM sodium chloride.
4) 4-6 mM KCl, 10-20 mM MgCl$_2$, 5-25 mM HEPES, 50-160 mM Na$_2$HPO$_4$/NaH$_2$PO$_4$ (pH 7.2) and 5-100 mM sodium lactobionate or 5-100 mM mannitol or 5-100 mM sodium succinate or 5-100 mM sodium chloride.
5) 4-6 mM KCl, 10-20 mM MgCl$_2$, 80-100 mM NaCl, 8-12 mM glucose, 0.3-0.5 mM Ca(NO$_3$)$_2$, 20-25 mM HEPES and 50-100 mM tris/HCl or 30-50 mM Na$_2$HPO$_4$/NaH$_2$PO$_4$ (pH 7.2)
6) 0.1-3.0 mM MgCl$_2$, 50-200 mM K$_2$HPO$_4$/KH$_2$PO$_4$ (pH 6.5) and/or 1-50 mM mannitol and/or 1-50 mM sodium succinate.

In an embodiment, the present invention provides a method for introducing biologically active molecules into animal or human cells by means of electric current which comprises suspending the cells and dissolving the biologically active molecules in a buffer solution, which has a buffer capacity of at least 20 mmol*l$^{-1}$*pH$^{-1}$ and an ionic strength of at least 200 mmol*l$^{-1}$ with a change in the pH from pH 7 to pH 8 and at a temperature of 25° C., and applying an electric voltage to the suspension. With the aid of this method, biologically active molecules can be introduced into animal and human cells by means of electroporation with transfection efficiencies up to 93% and at the same time with low cell mortality. Various cell types, especially quiescent and weakly dividing cells can be successfully transfected.

The buffer solution according to the invention is suitable for carrying out an electroporation method in which biologically active molecules are introduced into the cells by a voltage pulse having a field strength of up to 2 to 10 kV*cm$^{-1}$ and a duration of 10 to 200 μs and a current density of at least 2 A*cm$^{-2}$. As a result of the high voltage pulse, it is possible for DNA to be transfected directly into the cell nucleus of animal and human cells with irreversible membrane damage being avoided by the shortness of the pulse. As a result of the shortness of the high-voltage pulse, the high ionic strength or conductivity of the buffer also does not result in any disadvantageous heating of the solution so that in addition to dividing cells, quiescent or weakly dividing cells can also be transfected with high efficiency and low mortality. The interaction of the high ionic strength of the buffer and short high-voltage pulses rather brings about efficient pore opening, wherein the strong buffer effect can also compensate for extreme fluctuations of the pH.

A current flow following the high-voltage pulse without interruption, having a current density of 2 to 14 A*cm$^{-2}$, preferably up to 5 A*cm$^{-2}$, and a duration of 1 to 100 ms, preferably up to 50 ms, can also be applied by using the buffer according to the invention in the method. The high buffer capacity of the buffer solution according to the invention reduces any change in the pH in the vicinity of the electrodes during the long-lasting second pulse, which contributes to the electrophoresis of the DNA, so that the cell mortality can be effectively reduced.

As a result of the method according to the invention, the transfection of biologically active molecules is thus optimised using the electric current in the cell nucleus of animal or human cells. In this case, nucleic acids, proteins or peptides can be introduced into quiescent or dividing animal or human cells with a high efficiency. The buffer solution according to the invention also favours the introduction of nucleic acids, proteins or peptides into primary cells by supporting high-voltage pulses.

The nucleic acids can also be present in the buffer solution in complexes or in compounds with peptides, proteins or other biologically active molecules.

The method according to the invention is also suitable for the transfection of primary human blood cells, pluripotent precursor cells of human blood, primary human fibroblasts and endothelial cells, as well as muscle cells or melanocytes.

The cells produced by the method according to the invention are suitable in an especially advantageous fashion for diagnostic and/or analytical methods and for the production of pharmaceutical products for ex-vivo gene therapy.

Table 1 gives specific compositions of buffer solutions according to the invention which are each optimised for different applications or cell types and have proved to be especially advantageous with reference to high transfection efficiencies and reducing cell mortality. However, other compositions may also be understood within the scope of the invention so that these examples also should not be understood as restrictive.

EXAMPLES

The following examples illustrate specific embodiments of the invention but should not be regarded as restrictive.

Example 1

Transfection Efficiency and Survival Rate of Primary Human Endothelial Cells

In order to study the transfection and survival rate of cells during electrotransfection as a function of the buffer capacity and the ionic strength, primary human endothelial cells were transfected with a vector coding for the heavy chain of the mouse MHC class 1 protein H-2K$^k$.

Respectively 7×10$^5$ cells with respectively 5 μg vector DNA and the respective electrotransfection buffer were placed at room temperature in a cuvette having an interelectrode gap of 2 mm and transfected by a 1000 V pulse of 100 μs duration. In addition, comparative values were determined using PBS (Phosphate Buffered Saline: 10 mM sodium phosphate, pH 7.2+137 mM NaCl, ionic strength=161.5 mM, buffer capacity=4.8 mM/pH). Directly after the electrotransfection the cells were washed out of the cuvette using 400 μl of culture medium, incubated for 10 minutes at 37° C. and then transferred to a culture dish with pre-heated medium. After incubating for 6 h, the cells were incubated with a Cy5-coupled anti-H-2K$^k$-antibody and analysed using a flow cytometer (FACScalibur, Becton Dickinson).

As can be seen from FIG. 1, both the transfection efficiencies and the survival rates increase with increasing buffer capacity and ionic strength. In each case significantly better values could be achieved compared with the PBS comparative solution in which an extremely high mortality rate occurred. In some buffer solutions the mortality rate was so high that these values could not be evaluated statistically.

Example 2

Transfection Efficiency and Survival Rate of Primary Human Lymphocytes

Furthermore, the transfection and survival rate of primary human lymphocytes during electrotransfection was studied as a function of the buffer capacity and the ionic strength. For this purpose respectively 5×10$^6$ cells with respectively 5 μg H-2K$^k$-expression vector-DNA in the respective buffers were placed at room temperature in a cuvette having a 2 mm interelectrode gap and electrotransfected by a 1000 V, 100 μs pulse followed by a current flow having a current density of 4 A*cm$^{-2}$ and 40 ms. In addition, comparative values were determined using PBS (ionic strength=161.5mM, buffer capacity=4.8 mM/PH). The analysis was made after 16 hours.

Figure 2:
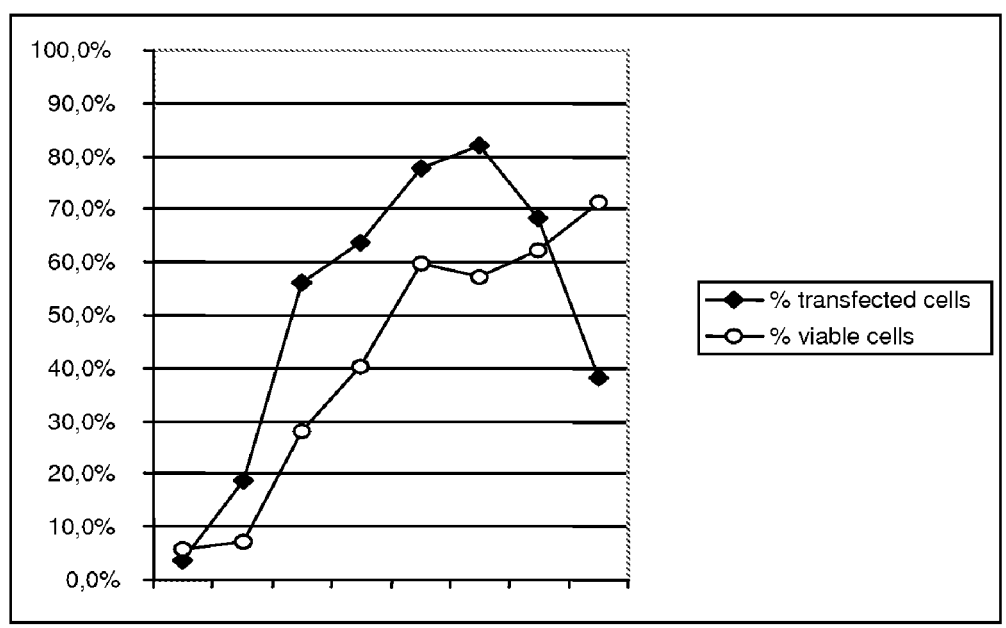
FIG. 2 is a graphical representation of the transfection efficiency and the survival rate for primary human lymphocytes as a function of the buffer capacity and ionic strength of the buffer solution.
Figure 2:
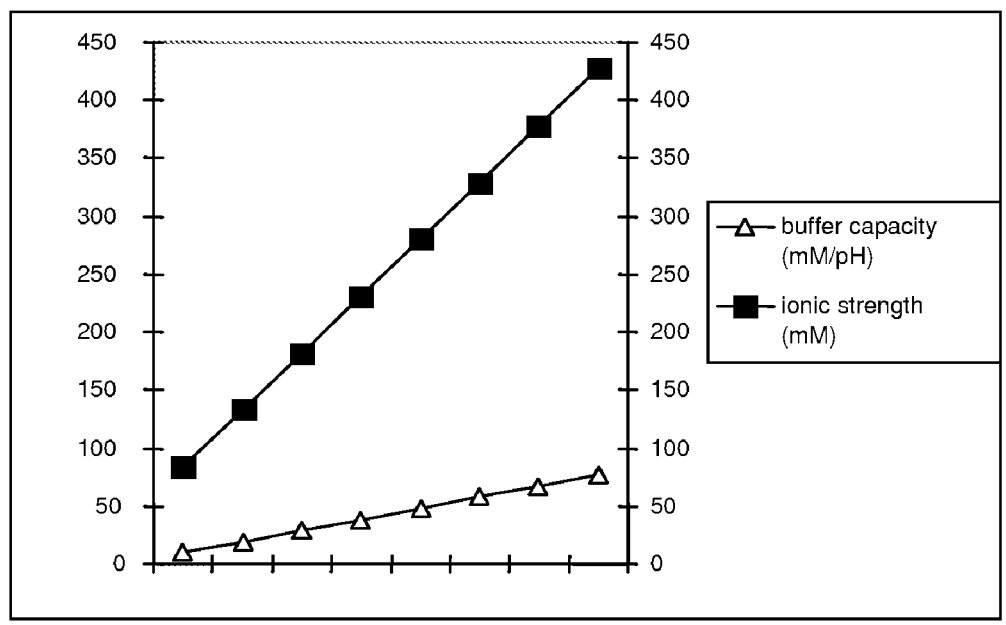

As can be seen from FIG. 2, it is clear that the survival rates of the cells increase as the buffer capacity and ionic strength of the buffer solutions used increases. In some cases significantly better values could be achieved compared with the comparative solution (PBS: 40.1% transfected cells 38.3% living cells). Here also the transfection efficiency can thus be increased significantly by the choice of suitable buffer solution according to the invention compared with conventional solutions, such as medium or PBS for example.

Example 3

Transfection of Primary Human Fibroblasts

Figure 3:
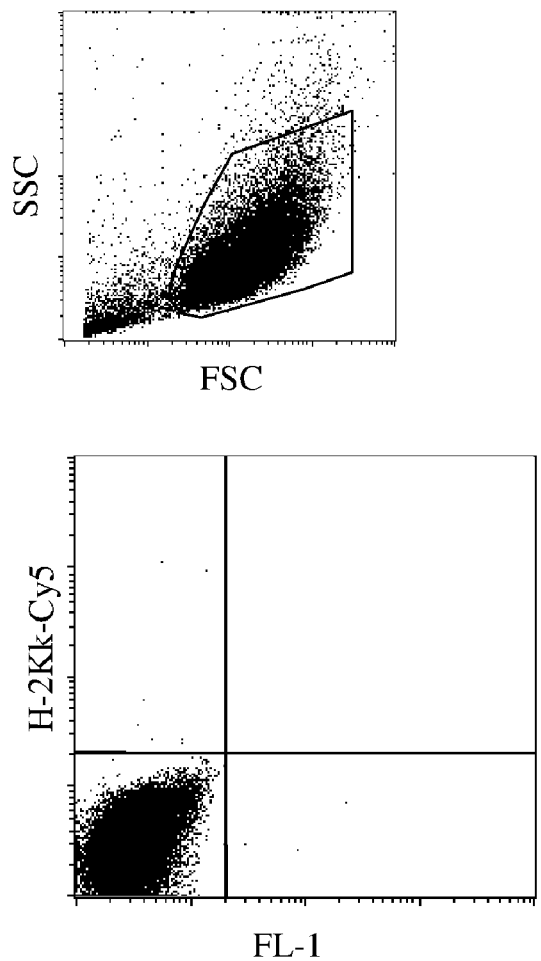
FIG. 3 shows a flow-cytometric analysis of primary human fibroblasts transfected with H-2K$^k$ expression vector during which the cells were incubated with a Cy5-coupled anti-H-2K$^k$ antibody and analysed using a flow cytometer (FACScalibur, Becton Dickinson) (FL-1, FL-2, FL-3=fluorescence channel 1, 2, 3; SSC=sideward scatter, FSC=forward scatter)
Figure 3:
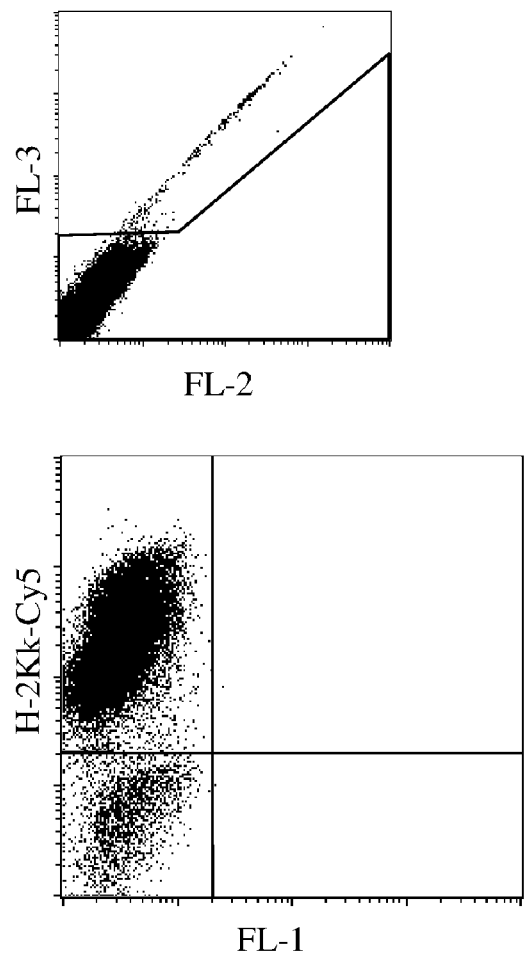

FIG. 3 shows an FACScan analysis of primary human fibroblasts transfected with H-2K$^k$ expression vector. 5×10$^5$ cells with 5 μg vector DNA in buffer 6 from Table 1 were placed at room temperature in a cuvette having a 2 mm interelectrode gap and transfected by a 1000 V, 100 μs pulse followed by a current flow of 6 A*cm$^{-2}$ and 33 ms. After incubating for 5 h, the cells were incubated with a Cy5-coupled anti-H-2K$^k$ antibody and analysed using a flow cytometer (FACScalibur, Becton Dickinson). The number of dead cells was determined by staining with propidium iodide. 93% of the living cells expressed the H-2K$^k$ antigen which corresponds to a very high transfection efficiency.

Example 4

Transfection of Human Smooth Muscle Cells

Figure 4:
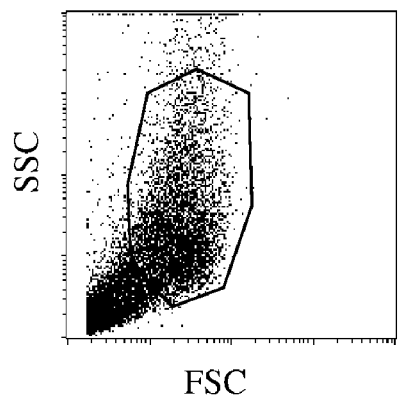
FIG. 4 shows a flow-cytometric analysis of human smooth muscle cells transfected with H-2K$^k$ expression vector during which the cells were incubated with a Cy5-coupled anti-H-2K$^k$ antibody and analysed using a flow cytometer (FACScalibur, Becton Dickinson) (FL-1, FL-2, FL-3=fluorescence channel 1, 2, 3; SSC=sideward scatter, FSC=forward scatter)
Figure 4:
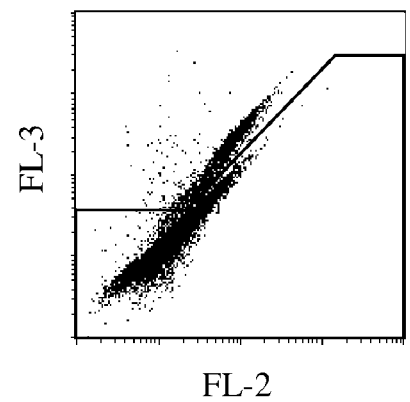
Figure 4:
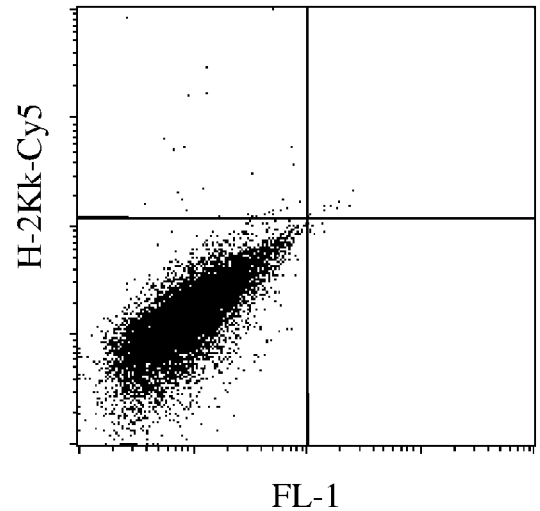
Figure 4:
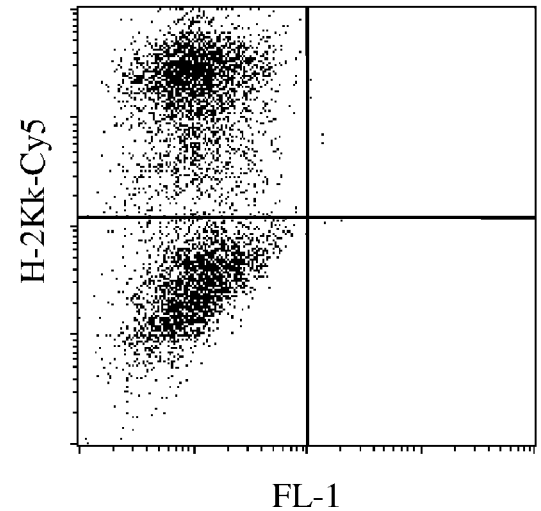

FIG. 4 shows an FACScan analysis of human smooth muscle cells transfected with H-2K$^k$ expression vector. $5\times10^5$ cells with 5 µg vector DNA in buffer 6 from Table 1 were placed at room temperature in a cuvette having a 2 mm interelectrode gap and transfected by a 1000 V, 100 µs pulse followed by a current flow having a current density of 5,6 A*cm$^{-2}$ and 40 ms. After incubating for 13.5 h the cells were incubated using a Cy5-coupled anti-H-2K$^k$ antibody and analysed using a flow cytometer (FACScalibur, Becton Dickinson). The number of dead cells was determined by staining with propidium iodide. 53.8% of the living cells expressed the H-2K$^k$ antigen which also corresponds to a high transfection efficiency.

Example 5

Transfection of Primary Human Melanocytes

Figure 5:
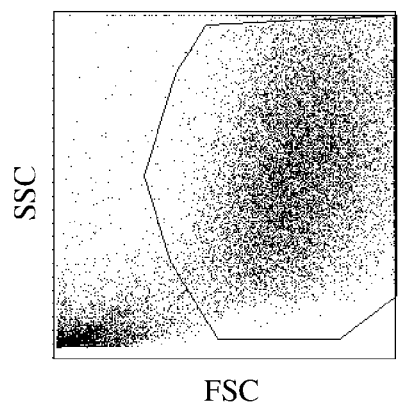
FIG. 5 shows a flow cytometric analysis of primary human melanocytes transfected with the GFP expression vector during which the cells were analysed using a flow cytometer (FACScalibur, Becton Dickinson) (FL-2, FL-3, FL-4=fluorescence channel 2, 3, 4; SSC=sideward scatter, FSC=forward scatter)
Figure 5:
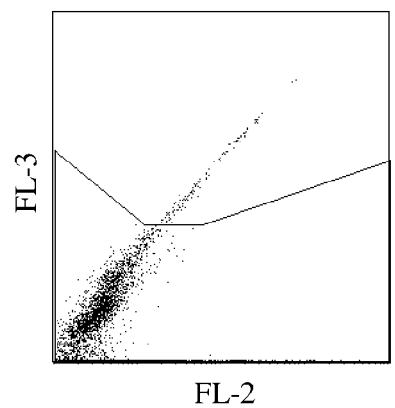
Figure 5:
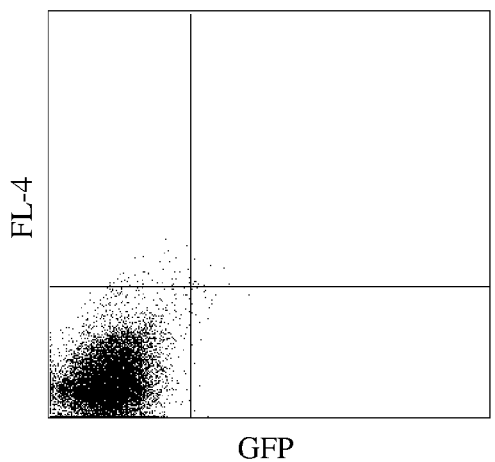
Figure 5:
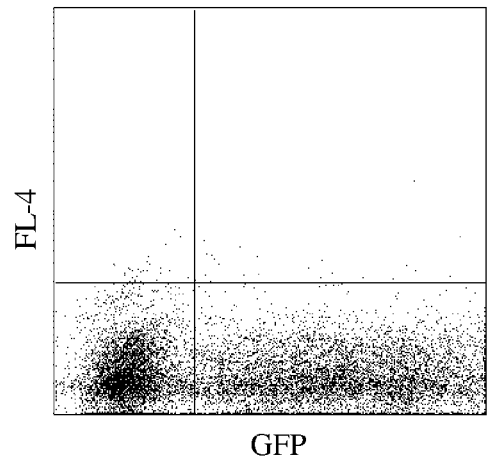

FIG. 5 shows an FACScan analysis of primary human melanocytes which were transfected with GFP expression vector. $5\times10^5$ cells with 5 µg pEGFP-C1 vector (Clontech Lab.) in buffer 40 from Table 1 were placed at room temperature in a cuvette having a 2 mm interelectrode gap and transfected by a 1000 V, 100 µs pulse followed by a current flow having a current density of 6 A*cm$^{-2}$ and 33 ms. After incubating for 24 h the cells were analysed using a flow cytometer (FACScalibur, Becton Dickinson). The number of dead cells was determined by staining with propidium iodide. 56.2% of the living cells expressed the GFP which also corresponds to a very high transfection efficiency.

Example 6

Transfection of Human CML Cell Line K562

Figure 6:
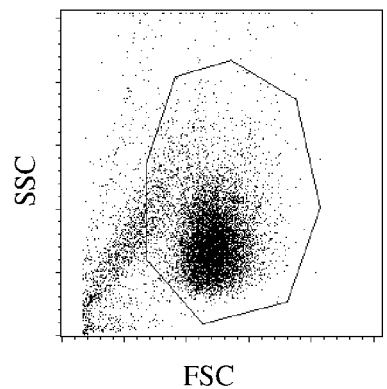
FIG. 6 shows a flow cytometric analysis of the human CML cell line K562 transfected with the GFP expression vector during which the cells were analysed using a flow cytometer (FACScalibur, Becton Dickinson) (FL-2, FL-3, FL-4=fluorescence channel 2, 3, 4; SSC=sideward scatter, FSC=forward scatter).
Figure 6:
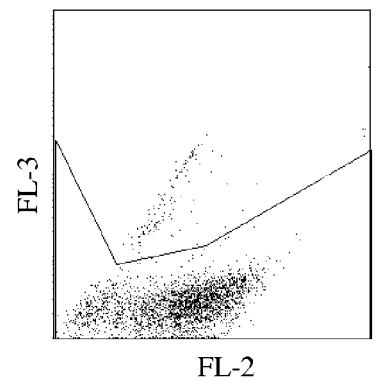
Figure 6:
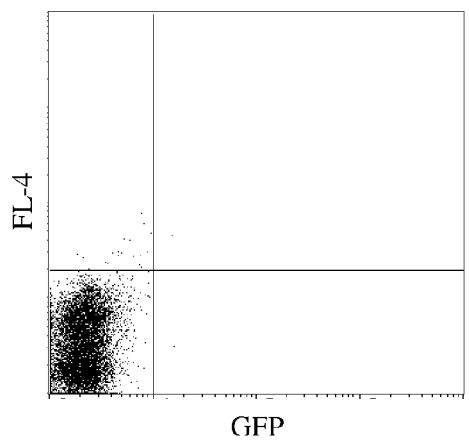
Figure 6:
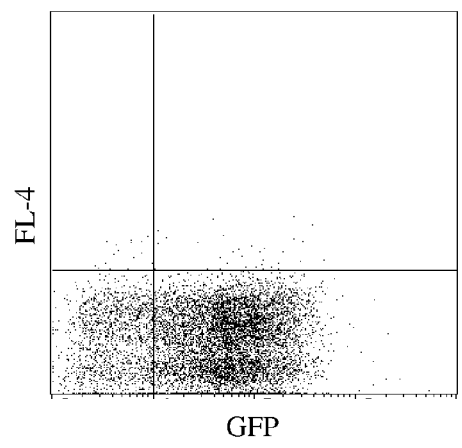

FIG. 6 shows an FACScan analysis of the human CML cell line K562 which was transfected with GFP expression vector. $5\times10^5$ cells with 5 µg pEGFP-C1 vector (Clontech Lab.) in buffer 42 from Table 1 were placed at room temperature in a cuvette having a 2 mm interelectrode gap and transfected by a 1000 V, 70 µs pulse followed by a current flow having a current density of 4 A*cm$^{-2}$ and 10 ms. After incubating for 24 h the cells were analysed using a flow cytometer (FACScalibur, Becton Dickinson). The number of dead cells was determined by staining with propidium iodide. 77.7% of the living cells expressed the GFP which also corresponds to a very high transfection efficiency.

List of Abbreviations Used

The following abbreviations were used in addition to those commonly used in Duden:
A Ampere
APC Allphycocyanin
CD Cluster of differentiation
cm Centimetre
DNA Deoxyribonucleic acid
FACScan Fluorescence activated cell scanning
FCS Foetal calf serum
FL Fluorescence
FSC Forward scatter
HEPES N-(2-hydroxyethyl)-piperazine-N'-(2-ethanesulphonic acid)
ml Millilitre
mM Millimolar
msec Millisecond
PBS Phosphate buffered saline
PE Phycoerythrin
PerCP Peridinin chlorophyll protein
pH negative common logarithm of the hydrogen ion concentration
RNA Ribonucleic acid
RPMI Rosewell Park Memorial Institute
SSC Sideward scatter
Tris Tris-(hydroxymethyl)-aminoethane-hydrochloride
µg Microgram
µl Microlitre
µsec Microsecond
V Volt

TABLE 1

| Buffer # | Na Phosphate [mmol/l] | K phospalite [mmol/l] | Mannitol [mmol/l] | KCl [mmol/l] | MgCl₂ [mmol/l] | HEPES[1] [mmol/l] | Na Succinate [mmol/l] | Glucose [mmol/l] | Na lacto-bionate [mmol/l] | NaCl [mmol/l] | K glutamate[1] [mmol/l] | Ca(NO₂)₃ [mmol/l] | others [mmol/l] | pH value | Peptide (μmol/l) |
|---|---|---|---|---|---|---|---|---|---|---|---|---|---|---|---|
| 1 | 30 | 0 | 0 | 5 | 10 | 20 | 0 | 11 | 0 | 100 | 0 | 0.42 | 0 | 7.2 | MEEDTPPKKKRKVEDL (SEQ ID NO:1), 25 μM |
| 2 | 30 | 0 | 0 | 5 | 10 | 20 | 0 | 11 | 0 | 100 | 0 | 0.42 | 0 | 7.2 | |
| 3 | 50 | 0 | 0 | 5 | 1 | 0 | 0 | 11 | 0 | 100 | 0 | 0 | 0 | 7.2 | MEEDTPPKKKRKVEDL (SEQ ID NO:1), 25 μM |
| 4 | 50 | 0 | 0 | 5 | 10 | 0 | 0 | 11 | 0 | 100 | 0 | 0 | 0 | 7.2 | |
| 5 | 50 | 0 | 0 | 5 | 10 | 0 | 0 | 11 | 0 | 100 | 0 | 0 | 0 | 7.2 | |
| 6 | 140 | 0 | 0 | 5 | 10 | 0 | 0 | 0 | 0 | 0 | 0 | 0 | 0 | 7.2 | MEEDTPPKKKRKVEDL (SEQ ID NO:1), 25 μM |
| 7 | 160 | 0 | 0 | 5 | 10 | 0 | 0 | 0 | 0 | 0 | 0 | 0 | 0 | 7.2 | |
| 8 | 120 | 0 | 40 | 5 | 10 | 0 | 0 | 0 | 0 | 0 | 0 | 0 | 0 | 7.2 | |
| 9 | 120 | 0 | 40 | 5 | 10 | 0 | 0 | 0 | 0 | 0 | 0 | 0 | 0 | 7.2 | |
| 10 | 100 | 0 | 80 | 5 | 10 | 0 | 0 | 0 | 0 | 0 | 0 | 0 | 0 | 7.2 | MEEDTPPKKKRKVEDL (SEQ ID NO:1), 25 μM |
| 11 | 90 | 0 | 0 | 5 | 10 | 20 | 0 | 0 | 0 | 0 | 0 | 0 | 0 | 7.2 | |
| 12 | 120 | 0 | 0 | 5 | 10 | 20 | 0 | 0 | 20 | 0 | 0 | 0 | 0 | 7.2 | |
| 13 | 120 | 0 | 0 | 5 | 10 | 20 | 0 | 0 | 20 | 0 | 0 | 0 | 0 | 7.2 | |
| 14 | 90 | 0 | 0 | 5 | 10 | 20 | 0 | 0 | 50 | 0 | 0 | 0 | 0 | 7.2 | MEEDTPPKKKRKVEDL (SEQ ID NO:1), 25 μM |
| 15 | 120 | 0 | 0 | 5 | 15 | 0 | 0 | 0 | 0 | 12.5 | 0 | 0 | 0 | 7.2 | |
| 16 | 120 | 0 | 0 | 5 | 20 | 0 | 0 | 0 | 0 | 5 | 0 | 0 | 0 | 7.2 | |
| 17 | 140 | 0 | 5 | 0 | 0 | 0 | 11.5 | 0 | 0 | 0 | 0 | 0 | 0 | 7.28 | |
| 18 | 0 | 150 | 5 | 0 | 2.5 | 0 | 9 | 0 | 0 | 0 | 0 | 0 | 0 | 6.49 | |
| 19 | 0 | 150 | 5 | 0 | 2.5 | 0 | 9 | 0 | 0 | 0 | 0 | 0 | 0 | 6.49 | |
| 20 | 0 | 150 | 0 | 0 | 0.5 | 0 | 11.5 | 0 | 0 | 0 | 0 | 0 | 50 mM betaine | 6.49 | |
| 21 | 90 | 0 | 5 | 0 | 10 | 20 | 0 | 0 | 0 | 0 | 0 | 0 | 50 mM betaine | 7.2 | |
| 22 | 30 | 0 | 0 | 0 | 10 | 20 | 0 | 11 | 0 | 100 | 0 | 0.42 | 0 | 7.2 | |
| 23 | 90 | 0 | 0 | 5 | 10 | 20 | 0 | 0 | 0 | 0 | 0 | 0 | 20 mM proline | 7.2 | |
| 24 | 110 | 0 | 0 | 5 | 10 | 0 | 0 | 11 | 0 | 0 | 0 | 0.42 | 20 mM proline | 7.2 | |
| 25 | 30 | 0 | 0 | 0 | 10 | 20 | 0 | 11 | 0 | 100 | 0 | 0.42 | 20 mM proline | 7.2 | |
| 26 | 30 | 0 | 0 | 5 | 10 | 20 | 0 | 11 | 0 | 100 | 0 | 0.42 | 20 mM citrate | 7.2 | |
| 27 | 30 | 0 | 0 | 5 | 10 | 20 | 0 | 11 | 0 | 100 | 0 | 0.42 | 200 mM ascorbate | 7.2 | |
| 28 | 30 | 0 | 0 | 5 | 10 | 20 | 0 | 11 | 0 | 100 | 0 | 0.42 | 0.2% DMSO | 7.2 | |
| 29 | 30 | 0 | 0 | 5 | 10 | 20 | 0 | 11 | 0 | 100 | 0 | 0.42 | 5 mM glutathione | 7.2 | |
| 30 | 30 | 0 | 0 | 5 | 10 | 20 | 0 | 11 | 0 | 100 | 0 | 0.42 | 2 mM NAD- | 7.2 | |

TABLE 1-continued

| Buffer # | Na Phosphate [mmol/l] | K phosphate [mmol/l] | Mannitol [mmol/l] | KCl [mmol/l] | MgCl$_2$ [mmol/l] | HEPES$^{1)}$ [mmol/l] | Na Succinate [mmol/l] | Glucose [mmol/l] | Na lactobionate [mmol/l] | NaCl [mmol/l] | K glutamate$^{1)}$ [mmol/l] | Ca(NO$_2$)$_3$ [mmol/l] | others [mmol/l] | pH value | Peptide (μmol/l) |
|---|---|---|---|---|---|---|---|---|---|---|---|---|---|---|---|
| 31 | 30 | 0 | 0 | 5 | 10 | 20 | 0 | 11 | 0 | 100 | 0 | 0.42 | 0.5% Ficoll 400 | 7.2 | z-VAD-FMK, 20 μM |
| 32 | 30 | 0 | 0 | 5 | 10 | 20 | 0 | 11 | 0 | 100 | 0 | 0.42 | 25 mM Dithiothreitol | 7.2 | |
| 33 | 30 | 0 | 0 | 5 | 10 | 20 | 0 | 11 | 0 | 100 | 0 | 0.42 | 0 | 7.2 | GKPTAKKQHSTPKKKRKVED (SEQ ID NO:2), 25 μM |
| 34 | 30 | 0 | 0 | 5 | 10 | 20 | 0 | 11 | 0 | 100 | 0 | 0.42 | 0 | 7.2 | PSSDDEATADSQHSTPPKKKRKVED (SEQ ID NO:6), 25 μM |
| 35 | 30 | 0 | 0 | 5 | 10 | 20 | 0 | 11 | 0 | 100 | 0 | 0.42 | 0 | 7.2 | (PNA)*-GKPTAKKQHSTPKKKRKVED, (SEQ ID NO:3), 25 μM |
| 36 | 30 | 0 | 0 | 5 | 10 | 20 | 0 | 11 | 0 | 100 | 0 | 0.42 | 0 | 7.2 | (PNA)*-PSSDDEATADSQHSTPPKKKRKVED (SEQ ID NO:4), 25 μM |
| 37 | 30 | 0 | 0 | 5 | 10 | 20 | 0 | 11 | 0 | 100 | 0 | 0.42 | 0 | 7.2 | |
| 38 | 50 | 0 | 0 | 5 | 10 | 20 | 0 | 11 | 0 | 100 | 0 | 0.4 | 0 | 7.24 | |
| 39 | 0 | 20 | 0 | 0 | 0 | 0 | 0 | 0 | 0 | 10 | 120 | 0 | 5 mM glutathione | | |
| 40 | 140 | 0 | 0 | 5 | 10 | 0 | 0 | 0 | 0 | 0 | 0 | 0 | 1 mM EDTA | 7.2 | MEEDTPPKKKRKVEDL (SEQ ID NO:1), 25 μM |
| 41 | 90 | 0 | 0 | 5 | 10 | 20 | 24 | 0 | 0 | 0 | 0 | 0 | 0 | 7.2 | |
| 42 | 90 | 0 | 0 | 5 | 10 | 20 | 24 | 0 | 0 | 0 | 0 | 0 | 0 | 7.2 | MEEDTPPKKKRKVEDL (SEQ ID NO:1), 25 μM |

*PNA(CTCTTCCTTTTC (SEQ ID NO:5))
$^{1)}$titrated with KOH

The invention claimed is:

1. A method for introducing biologically active molecules into animal or human cells using an electric current, comprising:
   (i) suspending the cells and dissolving the biologically active molecules in a buffer solution comprising HEPES and at least 10 mmol×l$^{-1}$ magnesium ions (Mg$^{2+}$), the buffer solution having a buffer capacity of at least 20 mmol×l$^{-1}$×pH$^{-1}$ at a change in the pH from pH 7 to pH 8 and at a temperature of 25° C., and an ionic strength of at least 200 mmol×l$^{-1}$, and
   (ii) applying an electric voltage to the suspension.

2. The method as recited in claim 1, wherein the applying an electric voltage to the suspension comprises a voltage pulse having a field strength between 2 and 10 kV×cm$^{-1}$, a duration of 10 to 200 μs, and a current density of at least 2 A×cm$^{-2}$.

3. The method as recited in claim 1, wherein the applying an electric voltage comprises a current flow following a high-voltage pulse without interruption, the current flow having a current density of 2 to 14 A×cm$^{-2}$, and a duration of 1 to 100 ms.

4. The method as recited in claim 1, wherein the biologically active molecules are transfected into a cell nucleus of the animal or human cells.

5. The method as recited in claim 1, wherein the biologically active molecules comprise at least one of nucleic acids, proteins and peptides and the animal or human cells include quiescent or dividing cells.

6. The method as recited in claim 5, wherein the nucleic acids are included in complexes or compounds comprising peptides, proteins or other biologically active molecules.

7. The method as recited in claim 1, wherein the biologically active molecules comprise at least one of nucleic acids, proteins and peptides and the animal or human cells include primary cells.

8. The method as recited in claim 7, wherein the nucleic acids are included in complexes or compounds comprising peptides, proteins or other biologically active molecules.

9. The method as recited in claim 1, wherein the cells comprise at least one of primary human blood cells, pluripotent precursor cells of human blood, primary human fibroblasts, endothelial cells, muscle cells and melanocytes.

* * * * *